US009074969B2

(12) United States Patent
Cooper

(10) Patent No.: US 9,074,969 B2
(45) Date of Patent: Jul. 7, 2015

(54) SAMPLE FLUID STREAM PROBE

(75) Inventor: John A. Cooper, Beaverton, OR (US)

(73) Assignee: Cooper Environmental Services LLC, Beaverton, OR (US)

( * ) Notice: Subject to any disclaimer, the term of this patent is extended or adjusted under 35 U.S.C. 154(b) by 597 days.

(21) Appl. No.: 13/450,169

(22) Filed: Apr. 18, 2012

(65) Prior Publication Data

US 2013/0276904 A1    Oct. 24, 2013

(51) Int. Cl.
*G01N 1/22* (2006.01)

(52) U.S. Cl.
CPC ...... *G01N 1/2258* (2013.01); *G01N 2001/2267* (2013.01)

(58) Field of Classification Search
None
See application file for complete search history.

(56) References Cited

U.S. PATENT DOCUMENTS

| | | | |
|---|---|---|---|
| 2,987,921 A | | 6/1961 | Kraftson et al. |
| 4,060,001 A * | | 11/1977 | Archerd .................... 73/863.11 |
| 4,653,334 A * | | 3/1987 | Capone ...................... 73/863.81 |
| 4,942,774 A | | 7/1990 | McFarland |
| 5,109,708 A * | | 5/1992 | Lawless ..................... 73/863.11 |
| 5,109,711 A | | 5/1992 | Wendt |
| 6,021,678 A | | 2/2000 | Vardiman et al. |
| 7,731,100 B2 | | 6/2010 | Walsh, Jr. |
| 8,028,934 B2 | | 10/2011 | Wurz et al. |
| 8,590,812 B2 | | 11/2013 | Wurz |
| 8,672,241 B2 | | 3/2014 | Wurz |
| 8,857,740 B2 | | 10/2014 | Wurz |
| 2002/0134174 A1 * | 9/2002 | Silvis et al. ................ 73/863.81 |
| 2002/0162335 A1 * | 11/2002 | Steinthorsson et al. ........ 60/776 |
| 2003/0133111 A1 * | 7/2003 | Yamaguchi .................. 356/336 |
| 2013/0068852 A1 | 3/2013 | Wurz et al. |
| 2014/0048615 A1 | 2/2014 | Wurz |
| 2014/0290340 A1 | 10/2014 | Murthy et al. |

OTHER PUBLICATIONS

Haglund, et al., "A Continuous Emission Monitor for Quantitative Measurement of PM10 Emissions from Stationary Sources", For Presentation at the Air & Waste Management Association's 93rd Annual Conference & Exhibition, Jun. 18-22, 2000, 15 Pages.
Cain, et al., "Qualitative and Quantitative Wind Tunnel Measurements of the Airflow Through a Shrouded Airborne Aerosol Sampling Probe", 1998, pp. 1157-1169, J. Aerosol Sci. vol. 29, No. 9.
Gong, et al., "A Predictive Model for Aerosol Transmission Through a Shrouded Probe", 1996, pp. 3192-3198, Environ. Sci. Technol., vol. 30, No. 11.
Jimenez, et al., "A Comparative Study of Different Methods for the Sampling of High Temperature Combustion Aerosols", 2005, pp. 811-821, Aerosol Science and Technology, vol. 39.

(Continued)

*Primary Examiner* — Robert R Raevis
(74) *Attorney, Agent, or Firm* — Goff Patent Law PLLC; Jared S. Goff

(57) ABSTRACT

A sample fluid stream in a probe apparatus may be redirected in a redirection area, and a flowing gas sheet may be directed into the redirection area. Additionally, a conduit downstream of a probe nozzle may define a reverse taper (where the conduit is wider downstream), a lip for collecting droplets that have collected on conduit walls, and/or re-entraining gas directed at collected droplets. Focusing gas may focus the sample fluid stream away from the walls of the conduit. Such focusing gas may be at different temperatures for different sections of the conduit. For example, the focusing gas may be a lower temperature near the probe inlet, and may be at a higher temperature to act as drying gas farther downstream.

33 Claims, 3 Drawing Sheets

(56) References Cited

OTHER PUBLICATIONS

Figure 1:
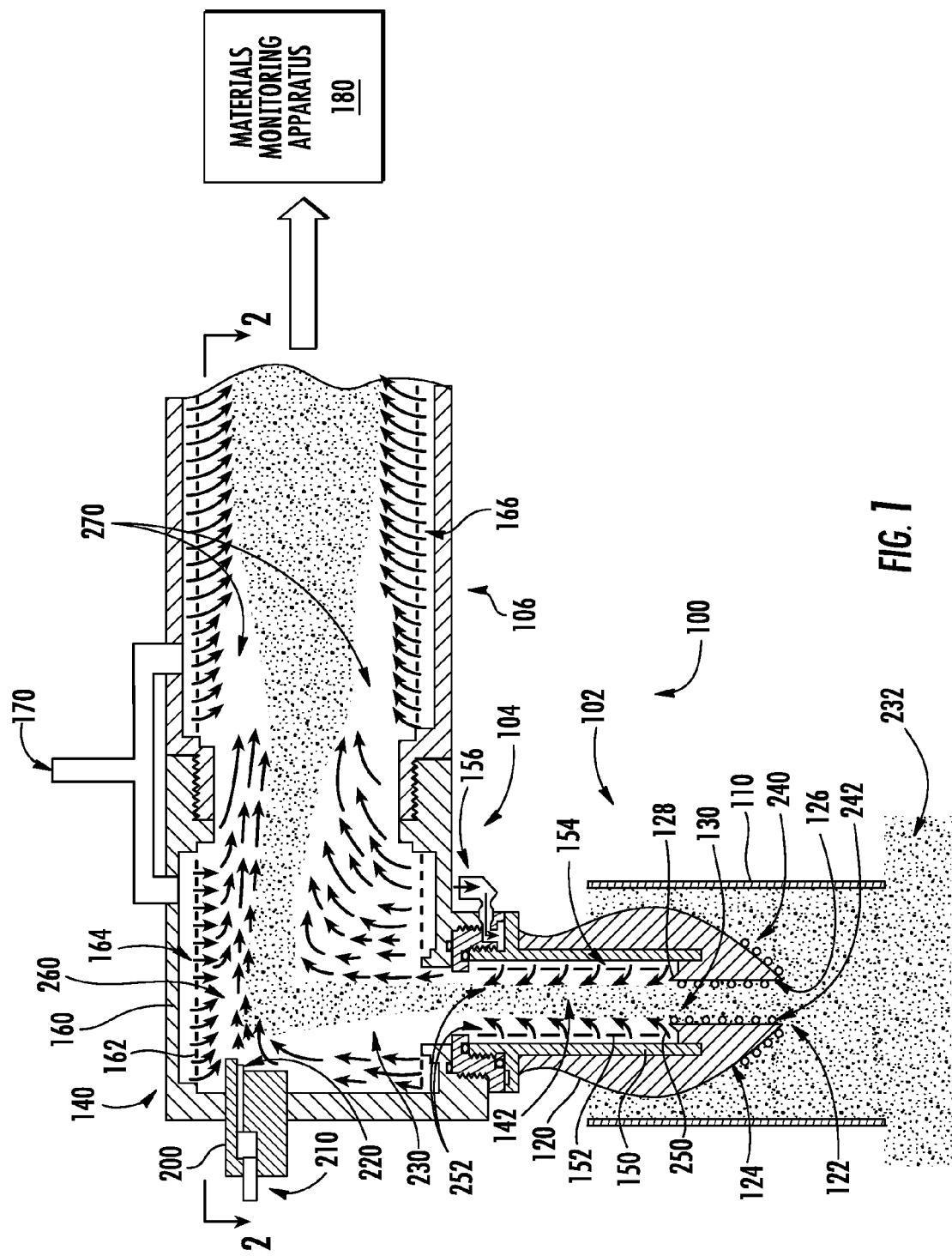
Figure 2:
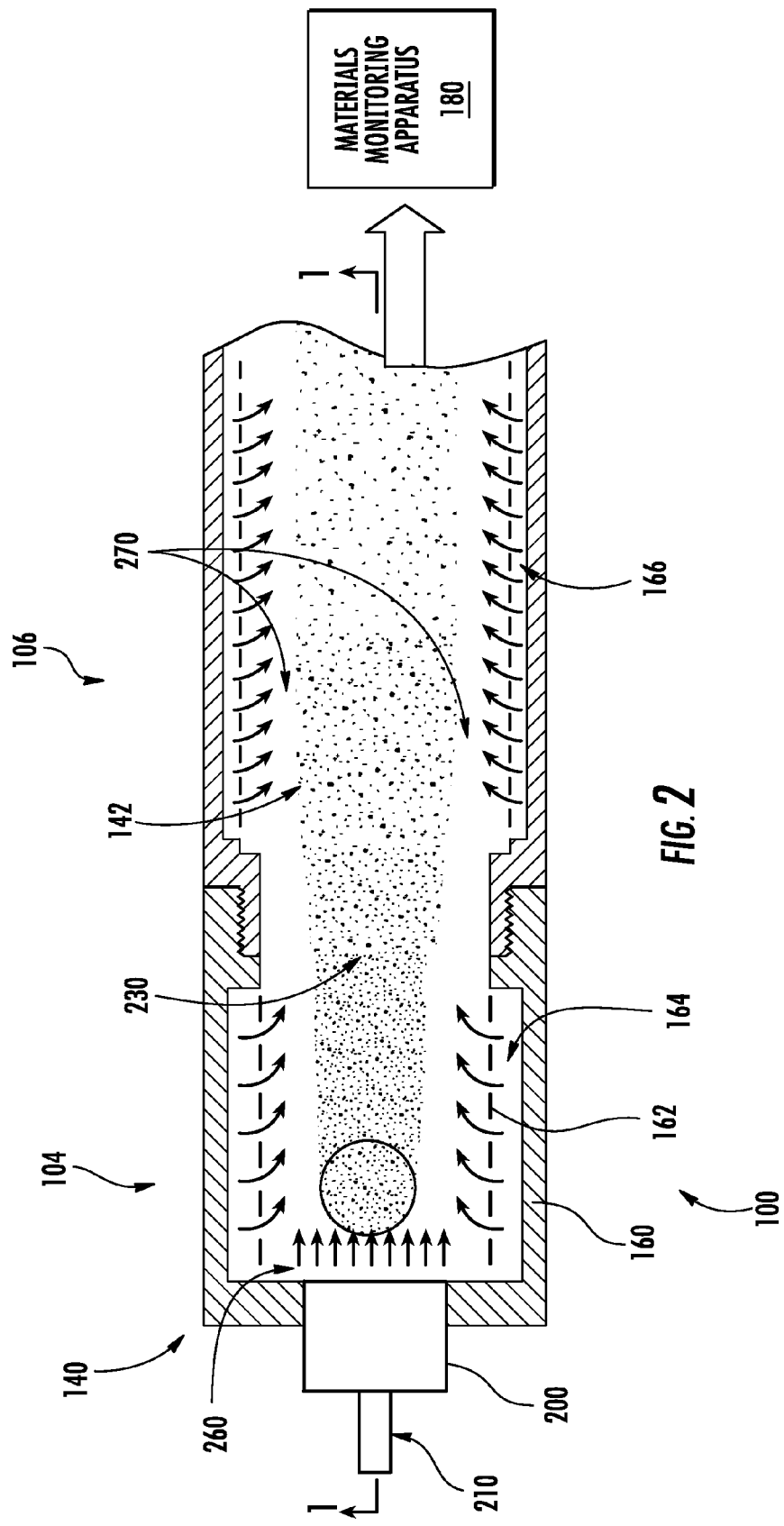
Figure 3:
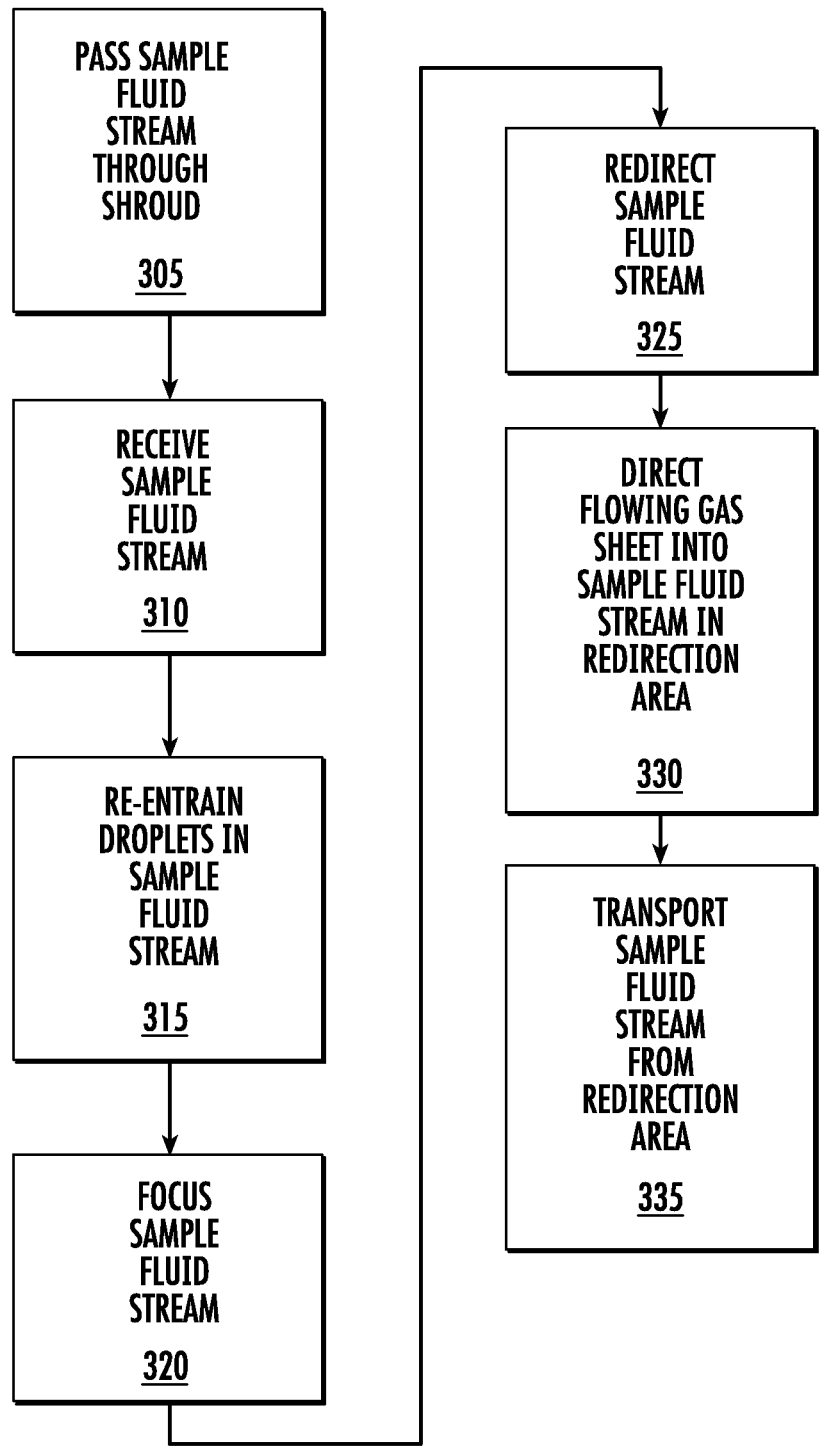

Podgorski, et al., "Numerical Analysis of the Airflow Hydrodynamics Near the Inlet to a Shrouded Probe for Sampling of Atmospheric Aerosol Particles at High Velocities", 2000, pp. S412-S413, J. Aerosol Sci., vol. 31, Suppl. 1.

McFarland, et al., "Single-Point Representative Sampling with Shrouded Probes", Aug. 1993, pp. 1-26.

Rodgers, et al., "Representative Sampling and Monitoring of Airborne Radioactive Effluent at Los Alamos National Laboratory", Revised: Aug. 1993, 99 Pages.

"Nozzle", Accessed at: <<http://en.wikipedia.org/wiki/Nozzle>>, Accessed on Jan. 15, 2015, 4 Pages.

* cited by examiner

SAMPLE FLUID STREAM PROBE

BACKGROUND

Probes can be used to collect sample fluid streams from main fluid streams. For example, probes can be used to collect sample fluid streams from stack emissions, such as wet stack emissions. Wet stacks are stacks containing main flows of emissions that are saturated with water vapor and have liquid water droplets that can vary from micro droplets typical of fogs (micrometers in diameter) to macro droplets typical of rain (millimeters in diameter). These droplets can contain a large fraction of particulate matter (PM) and metals associated with health effects. It can be difficult to collect a representative sample of these droplets for analysis on a continuous basis. Currently, continuous emission monitor systems (CEMS) use large diameter probes to reduce deviations from isokinetic sampling, avoid heating sampling probes to minimize dried salt plugs, use steam and compressed air "blow back" to prevent probe build up and plugging, or other similar techniques to allow continuous operations.

SUMMARY

Current probes can be ineffective in transporting a representative total stack aerosol sample to a CEMS. The description herein is directed to tools and techniques for probe apparatuses for collecting and transporting sample fluid streams. For example, a sample fluid stream may be redirected in a redirection area, and a flowing gas sheet may be directed into the redirection area. Such a gas sheet may provide one or more of various benefits, such as redirecting the flow while reducing impact of the flow with conduit walls, mixing the flow to promote drying, breaking up large droplets in the flow to promote drying, etc. Additionally, a conduit downstream of a probe nozzle may define a reverse taper (where the conduit is wider downstream), a lip for collecting droplets that have collected on conduit walls, and/or re-entraining gas directed at collected droplets. Such features can aid in decreasing impaction of droplets on the conduit walls and/or re-entraining collected droplets into the sample fluid stream. As another example, focusing gas may focus the sample fluid stream away from the walls of the conduit. Such focusing gas may be at different temperatures for different sections of the conduit. For example, the focusing gas may be a lower temperature near the probe inlet (which may decrease overheating of the probe nozzle, which could cause increased evaporation of droplets on the nozzle), and may be at a higher temperature to act as drying gas farther downstream. Such tools and techniques and/or others discussed below may be used alone or in combination.

This Summary is provided to introduce a selection of concepts in a simplified form. The concepts are further described below in the Detailed Description. This Summary is not intended to identify key features or essential features of the claimed subject matter, nor is it intended to be used to limit the scope of the claimed subject matter. Similarly, the invention is not limited to implementations that address the particular techniques, tools, environments, disadvantages, or advantages discussed in the Background, the Detailed Description, or the attached drawings.

BRIEF DESCRIPTION OF THE DRAWINGS

FIG. 1 is a side sectional view of a probe apparatus and taken along line 1-1 in FIG. 2, with a materials monitoring apparatus illustrated schematically.

FIG. 2 is a top sectional of the probe apparatus of FIG. 1 taken along line 2-2 in FIG. 1, with the materials monitoring apparatus again illustrated schematically.

FIG. 3 is a flowchart illustrating a probe technique.

The description and drawings may refer to the same or similar features in different drawings with the same reference numbers.

DETAILED DESCRIPTION

The probe features discussed herein include many new features that may be used alone or in combination. For example, the probe apparatus can use high velocity gas to redirect the flow of stack gas, particles and liquid droplets from the original direction of the stack gas to a direction towards the containment walls where the aerosol can be sampled or analyzed. For example, the high velocity gas can be in the form of a gas sheet, which can have a width that is at least ten times, at least fifty times, at least one-hundred times, at least five-hundred times, or at least one-thousand times a thickness of the gas sheet at an outlet of a gas knife. Other features can relate to reducing impaction of aerosol components in the sample fluid stream on conduit walls, encouraging re-entrainment of liquid deposited on walls of the inlet nozzle, etc. The various aspects of such features will now be discussed with reference to FIGS. 1-2.

Referring to FIG. 1, a probe apparatus (100) is illustrated. The probe apparatus (100) can include a nozzle area (102), a redirection area (104) downstream of the nozzle area (102), and a transport area (106) downstream of the redirection area (104). For example, the nozzle area (102) may be oriented vertically, with the redirection area (104) turning ninety degrees, and the transport area (106) extending horizontally from the redirection area (104). The nozzle area (102) can include a shroud (110), which can be mounted on a nozzle (120). The shroud (110) can be a tube that is connected to the nozzle (120) with circumferentially spaced beams (not shown) extending between the nozzle (120) and the shroud (110) to mount the shroud on the nozzle.

The nozzle (120) can have a nozzle inlet (122) defined by a leading edge of the nozzle (120). The nozzle inlet (122) can be centrally located within the shroud (110). The nozzle inlet (122) can have a diameter that is substantially smaller than an inner diameter of an entrance to the shroud (110) (e.g., from 0.1 to 0.4 times the diameter of the shroud (110)). For example, the nozzle inlet may have a diameter of about three-fourths of an inch and the shroud may have an inner diameter of about three inches. The nozzle can have an outer surface (124) that can slope outward downstream of the inlet (122). An inner surface (126) of the nozzle (120) can extend downstream from the nozzle inlet (122). The inner surface (126) can have a constant diameter for some length (e.g., for between 1/16 inch to 1/4 inch, or 1/8 inch), and can end in a lip (128). From the lip (128), the inner surface (126) can form a reverse taper (130). The reverse taper (130) can extend outward at any of various different angles, such as an angle less than ninety degrees and/or an angle greater than ninety degrees.

A main conduit (140) can extend back from the nozzle inlet (122), defining a stream area (142) where the sample fluid stream is to flow, as will be discussed more below. The main conduit (140) can include the nozzle (120) and the other conduit components discussed below (e.g., the outer non-porous and inner porous conduit components).

A downstream portion of the nozzle (120) can fit over at least a portion of a first outer non-porous conduit component (150) or can otherwise be secured to the non-porous conduit component (150). The first outer non-porous conduit component (150) can surround a first inner porous conduit component (152) to form a first annular gas chamber (154) between the components (150). A focusing gas source (156) can be connected in fluid communication with the first gas chamber (154). The first outer non-porous conduit component (150) can be sealed to the first inner porous conduit component (152). This seal may not be an entirely gas-tight seal, but it can be sealed sufficiently to force focusing gas to pass through the first inner porous conduit component (152). The focusing gas source (156) can provide focusing gas that is at a temperature at or below the temperature of the main fluid stream entering the nozzle (120).

Downstream of the nozzle area (102), the stream area (142) can continue and the main conduit (140) can include a second outer non-porous conduit component (160) surrounding a second inner porous conduit component (162) to form a second annular gas chamber (164) between the second outer non-porous conduit component (160) and the second inner porous conduit component (162). A drying gas source (170) can be connected in fluid communication with the second gas chamber (164). The second outer non-porous conduit component (160) can be sealed to the first inner porous conduit component (162). This seal may not be an entirely gas-tight seal, but it can be sealed sufficiently to force focusing gas to pass through the first inner porous conduit component (162). The focusing gas source (156) can provide focusing gas that is also heated to act as drying gas. Accordingly, the drying gas can be at a temperature that is above the temperature of the main fluid stream entering the nozzle (120). The second gas chamber (164) can extend along the redirection area (104) and along the transport area (106), providing drying gas through the second inner porous conduit component (162). The second gas chamber (164) may be interrupted by a joint in the main conduit (140), so that there is also a third gas chamber (166) that can also supply drying gas. There may also be additional gas chambers to supply drying gas and/or unheated focusing gas downstream of the third gas chamber (166), leading to a materials monitoring apparatus (180) shown schematically in FIGS. 1 and 2. The materials monitoring apparatus (180) may be any of various types that are able to test the nature and/or quantity of particles in the sample stream flowing through the probe apparatus (100). For example, the monitoring apparatus (180) may be an X-ray fluorescence testing apparatus.

Additionally, the probe apparatus (100) can include a gas knife (200) that can be connected to a pressurized gas source (210). The gas knife (200) can define a gap that acts as an outlet (220) through which the pressurized gas can be forced to form a high velocity sheet of flowing gas. The outlet (220) may be curved so that the gas sheet is also curved. For example, the outlet (220) can form a concave curve from the perspective of the nozzle (120). Accordingly, the curve of the outlet (220) may match the curve of the conduit (140) distal from the nozzle (120) in FIGS. 1-2. The curve may have radius of curvature that is the same as a radius of the main conduit (140) in the redirection area (104), and the curve may extend through a radial arc of from forty-five to one-hundred and eighty degrees, such as from ninety degrees to one-hundred and twenty degrees. The outlet (220) can have a width that is greater than a diameter of the sample stream flowing into the redirection area (104), and the outlet (220) can have a thickness that is less than the width. For example, the outlet (220) can have can have a width that is at least ten times, at least fifty times, at least one-hundred times, at least five-hundred times, or at least one-thousand times a thickness of the outlet (220). For example, outlet (220) may be one and one-half inches wide, and one one-thousandth of an inch thick (from top to bottom). The outlet (220) of the gas knife (200) can be directed into the redirection area (104). The outlet (220) can be pointed in a different direction from the direction of the flow into the nozzle inlet (122) and into the redirection area (104). For example, the outlet (220) can be pointed in the same direction as the direction of the main conduit (140) downstream of the redirection area (104). If the conduit makes a ninety-degree turn so that the main conduit (140) downstream of the redirection area (104) is at a right angle to the nozzle (120), the outlet (220) of the gas knife (200) may also be directed at that same right angle.

Various different materials and/or manufacturing methods may be used in the components of the probe apparatus (100). For example, the components may be made of corrosive-resistant metals such as stainless steel, titanium, or aluminum. Additionally, lightweight metals such as aluminum may be coated with corrosive-resistant coatings. The inner porous conduit components (152 and 162) may be sintered material such as sintered stainless steel.

Operation of the probe apparatus (100) will now be discussed with reference to a flowchart illustrated in FIG. 3, and still with reference to FIGS. 1-2. A sample fluid stream (230) from a main fluid stream (232) can be passed (305) through the shroud (110) and then received (310) through the nozzle (120) of the probe apparatus (100). The shroud (110) can slow the velocity of the fluid stream that passes through the shroud (110). This can create non-isokinetic flow around the edges of the shroud (110), which may cause a disproportionate number of particular sized particles to enter the shroud (e.g., disproportionately more large particles such as droplets). However, the flow around the edge of the shroud (110) can pass by the nozzle (120) without entering the nozzle inlet (122). The sample fluid stream (230) that enters the nozzle inlet (122) can be from the center of the shroud (110), where the non-isokinetic effects of the shroud can be reduced or non-existent. Additionally, the slowed velocity within the shroud (110) can reduce the non-isokinetic effects of the nozzle (120) on the sample fluid stream (230) entering the nozzle inlet (122). Additionally, the slowed velocity can reduce the rate of capture of the sample fluid stream (230), so that there can be less flow to be transported and analyzed.

The sample fluid stream (230) can travel into the nozzle (120) in a first direction. Some droplets (240) from the main fluid stream (232) that are not in the sample fluid stream (230) may collect on the outer surface (124) of the nozzle (120). Other droplets (242) in the sample fluid stream (230) may impact and collect on the inner surface (126) of the nozzle (120). Such droplets (242) can be forced farther into the nozzle (120) by the flow of the sample fluid stream (230). These droplets (242) can be re-entrained (315) in the sample fluid stream (230). For example, the droplets (242) may collect on the lip (128) that is upstream of at least a portion of the reverse taper (130). A re-entraining gas flow (250) (e.g., part of a flow of focusing gas (252) from the first gas chamber (154)) can be directed along a flow path to the droplets (242), such as by flowing along the lip (128) and carrying the droplets (242) back into the sample fluid stream (230).

The focusing gas (252) passing through the first inner porous conduit component (152) can also be directed into the sample fluid stream (230) from multiple different sides (e.g., from all around the sample fluid stream (230) so that the focusing gas (252) surrounds the sample fluid stream (230)) to focus (320) the sample fluid stream into a central area away from the surrounding walls of the first inner porous conduit component (152). This focusing (320) can reduce impaction of droplets and/or dry particles from the sample fluid stream (230) from impacting walls of the main conduit (140). Additionally, the reverse taper (130) brings the walls of the main conduit (140) out and away from the sample fluid stream (230), which can also reduce impaction of droplets and/or dry particles from the sample fluid stream (230) on walls of the main conduit (140).

The sample fluid stream (230) can be redirected (325) in the redirection area (104) from the first sample fluid stream direction to a second sample fluid stream direction. A flowing gas sheet (260) can be directed (330) into the sample fluid stream (230) in the redirection area (104), such as through the gas knife (200). The gas sheet (260) can be traveling in a sheet direction that is different from the first sample fluid stream direction. The gas sheet (260) can redirect at least a portion of the sample fluid stream (230) in the redirection area (104). The gas sheet (260) may also break liquid droplets in the sample fluid stream (230), which can promote drying of such droplets. Additionally, the gas sheet (260) can mix a central portion of the sample fluid stream (230) (which can be cooler and wetter than the rest of the sample fluid stream (230)) with other portions of the sample fluid stream (230). This may also promote drying of the overall sample fluid stream (230).

The gas sheet (260) can be wider than the sample fluid stream (230). Also, the gas sheet (260) may be curved and have a high velocity. For example, a velocity of the gas sheet (260) may be greater than a velocity of the sample fluid stream (230). For example, the main fluid stream (232) may be flowing with a velocity of about twenty to about sixty miles per hour, and this velocity may be cut in half in the shroud (110) before the sample fluid stream (230) enters the nozzle inlet (122). The gas sheet (260) may have a velocity that is from fifty to two-hundred miles per hour, such as from one-hundred mile per hour to one-hundred and fifty miles per hour. The source of gas for the gas sheet (260) can be heated so that the gas sheet may be at an elevated temperature, such as a temperature above two-hundred and twelve degrees Fahrenheit, such as 250 degrees Fahrenheit.

The sample fluid stream can be transported (335) from the redirection area (104), such as to the materials monitoring apparatus (180). As noted above, the sample fluid stream (230) can be focused, such as using focusing gas (252). The focusing gas (252) in a first section (e.g., the nozzle area (102)) can be a lower temperature than focusing gas in a second section (e.g., the redirection area (104) and/or the transport area (106)) downstream of the first section. For example, the focusing gas in the second section can be drying gas (270), which can be supplied through the second gas chamber (164) and possibly through subsequent gas chambers (e.g., the third gas chamber (166)). This drying gas (270) can focus the sample fluid stream (230) in the redirection area (104) and/or the transport area (106). The drying gas (270) may be heated to an elevated temperature similar to the temperature of the gas sheet (260). Such high temperatures can heat the sample fluid stream (230) and promote drying of droplets in the sample fluid stream (230). The gases discussed above may be air and/or one or more other gases.

The subject matter defined in the appended claims is not necessarily limited to the benefits described herein. A particular implementation of the invention may provide all, some, or none of the benefits described herein. Although operations for the various techniques are described herein in a particular, sequential order for the sake of presentation, it should be understood that this manner of description encompasses rearrangements in the order of operations, unless a particular ordering is required. For example, operations described sequentially may in some cases be rearranged or performed concurrently. Techniques described herein with reference to flowcharts may be used with one or more of the systems described herein and/or with one or more other systems. Moreover, for the sake of simplicity, flowcharts may not show the various ways in which particular techniques can be used in conjunction with other techniques.

While the invention has been particularly shown and described with reference to preferred embodiments thereof, it will be understood by those skilled in the art that various changes in form and details may be made therein without departing from the spirit and scope of the invention.

I claim:

1. A method comprising:

receiving a sample fluid stream from a main fluid stream through a nozzle of a probe apparatus located at least partially in the main fluid stream, the sample fluid stream traveling into the nozzle in a first fluid stream direction;

redirecting the sample fluid stream from the first fluid stream direction to a second fluid stream direction in a redirection area; and directing a flowing gas sheet into the sample fluid stream in the redirection area, the gas sheet traveling in a sheet direction that is different from the first direction; and focusing the sample fluid stream by directing focusing gas at the sample fluid stream from multiple different sides of the sample fluid stream.

2. The method of claim 1, wherein the gas sheet redirects at least a portion of the sample fluid stream in the redirection area.

3. The method of claim 1, wherein the gas sheet breaks liquid droplets in the sample fluid stream.

4. The method of claim 1, wherein the gas sheet mixes a central portion of the sample fluid stream with one or more other portions of the sample fluid stream.

5. The method of claim 4, wherein the central portion of the sample fluid stream is wetter than the one or more other portions of the sample fluid stream as the sample fluid stream enters the redirection area.

6. The method of claim 5, wherein the central portion of the sample fluid stream is cooler than the one or more other portions of the sample fluid stream as the sample fluid stream enters the redirection area.

7. The method of claim 1, wherein the gas sheet is wider than the sample fluid stream.

8. The method of claim 1, wherein the gas sheet is curved.

9. The method of claim 1, wherein a velocity of the gas sheet is greater than a velocity of the sample fluid stream.

10. The method of claim 1, further comprising re-entraining droplets from the sample fluid stream that impact an inner surface of the nozzle back into the sample fluid stream.

11. The method of claim 10, wherein re-entraining comprises directing a re-entraining gas flow at the droplets.

12. The method of claim 11, wherein the re-entraining gas flow passes along an edge that collects the droplets.

13. The method of claim 1, wherein a width of the gas sheet is at least ten times a thickness of the gas sheet as the gas sheet enters the redirection area.

14. The method of claim 13, wherein the width of the gas sheet is at least fifty times the thickness of the gas sheet as the gas sheet enters the redirection area.

15. The method of claim 1, wherein the focusing gas surrounds the sample fluid stream.

16. The method of claim 1, wherein the focusing gas in a first section is a lower temperature than the focusing gas in a second section downstream of the first section.

17. The method of claim 1, further comprising passing a body of fluid through at least a portion of a shroud positioned within the main fluid stream such that a first portion of the main fluid stream passes into the shroud to become the body of fluid while a second portion of the main fluid stream passes around the shroud, wherein receiving the sample fluid stream through the nozzle of the probe apparatus comprises receiving the sample fluid stream from the body of fluid after the body of fluid has passed through the at least a portion of the shroud.

18. A probe apparatus comprising:
a nozzle inlet portion configured to receive a sample fluid stream of a main fluid stream;
a conduit in fluid communication with the nozzle inlet portion, the conduit comprising a redirection area downstream of the nozzle inlet portion, the redirection area comprising a turn in the conduit, the conduit being a main conduit that comprises a first porous conduit component surrounded by and sealed to a first non-porous conduit component to define a first gas chamber between the first porous conduit component and the first non-porous conduit component and a stream flow area within the first porous conduit component;
a first pressurized gas source in communication with the first chamber; and
an outlet pointed into the redirection area, the apparatus being configured so that pressurized gas passing through the outlet forms a gas sheet that meets the sample fluid stream in the redirection area, with the gas sheet and the sample fluid stream traveling in different directions relative to each other until the gas sheet and the sample fluid stream meet in the redirection area.

19. The apparatus of claim 18, wherein the outlet comprises a curved gas sheet outlet.

20. The apparatus of claim 18, wherein a reverse taper portion is between the nozzle inlet portion and the redirection area, and the apparatus further comprises a flow path configured to direct re-entraining gas at an edge upstream of the reverse taper portion.

21. The apparatus of claim 18, wherein:
the main conduit further comprises a second porous conduit component surrounded by and sealed to a second non-porous conduit component to define a second chamber between the second porous conduit component and the second non-porous conduit component and the stream flow area within the second porous conduit component; and
the apparatus further comprises a second pressurized gas source in communication with the second chamber.

22. The apparatus of claim 21, wherein the first gas source is a source of gas at a first temperature, and the second gas source is a source of gas at a second temperature that is higher than the first temperature.

23. The apparatus of claim 18, further comprising a shroud with a leading edge upstream of the nozzle inlet portion, the shroud having an entrance that is larger than the nozzle inlet portion.

24. A probe apparatus comprising:
a nozzle inlet portion configured to receive a sample fluid stream of a main fluid stream; and
a conduit in fluid communication with the nozzle inlet portion, a reverse taper portion being downstream of the nozzle inlet portion, the conduit comprising a porous conduit component surrounded by and sealed to a non-porous conduit component to define a gas chamber between the porous conduit component and the non-porous conduit component and to define a stream area within the porous conduit component, the porous conduit component and the non-porous conduit component being downstream of the reverse taper portion.

25. The apparatus of claim 24, further comprising a source of re-entraining gas directed at droplets collected on the nozzle upstream of at least a portion of the reverse taper portion.

26. The apparatus of claim 25, wherein the re-entraining gas is directed at an edge upstream of at least a portion of the reverse taper portion.

27. The apparatus of claim 24, wherein the conduit comprises a redirection area downstream of the reverse taper portion, the redirection area comprising a turn in the conduit.

28. The apparatus of claim 27, further comprising an outlet pointed into the redirection area, the apparatus being configured so that pressurized gas passing through the outlet forms a gas sheet that meets the sample fluid stream in the redirection area.

29. The apparatus of claim 28, wherein the outlet comprises a curved gas sheet outlet.

30. The apparatus of claim 24, further comprising a pressurized gas source in communication with the gas chamber.

31. The apparatus of claim 30, wherein the chamber is a first gas chamber, the gas source is a first gas source, the porous conduit component is a first porous conduit component, the non-porous conduit component is a first non-porous conduit component, the stream area is a first stream area, and the conduit further comprises a second porous conduit component surrounded by and sealed to a second non-porous conduit component to define a second gas chamber that is downstream of the first gas chamber and to define a second stream area within the second porous conduit component, and wherein the apparatus further comprises a second pressurized gas source in communication with the second gas chamber.

32. The apparatus of claim 31, wherein the first gas source is a gas source of gas at a first temperature, and the second gas source is a source of gas at a second temperature that is higher than the first temperature.

33. The apparatus of claim 24, further comprising a shroud with a leading edge upstream of the nozzle inlet portion, the shroud having an entrance that is larger than the nozzle inlet portion.

* * * * *